United States Patent [19]

Dhawan et al.

[11] Patent Number: 5,092,876
[45] Date of Patent: Mar. 3, 1992

[54] CELL ATTACHMENT PEPTIDES DERIVED FROM AMYLOID P COMPONENT

[75] Inventors: Subhash Dhawan, Gaithersburg; Frank A. Robey, Bethesda, both of Md.

[73] Assignee: The United States of America as represented by the Department of Health and Human Services, Washington, D.C.

[21] Appl. No.: 400,870

[22] Filed: Aug. 30, 1989

[51] Int. Cl.[5] .......................... A61F 2/02; A61K 37/02
[52] U.S. Cl. ......................................... 623/11; 623/66; 530/327
[58] Field of Search ........................ 623/11, 12, 1, 66; 530/327, 328, 329, 330; 435/240.1, 240.2, 240, 243

[56] References Cited

U.S. PATENT DOCUMENTS 4,504,585 3/1985 Reynolds .
4,578,079 3/1986 Ruoslahti et al. .
4,589,881 5/1986 Pierschbacher et al. .
4,782,014 11/1988 Serban et al. .
4,792,525 12/1988 Ruoslahti et al. .

OTHER PUBLICATIONS

Ohnishi et al., "Isolation and Characterization of the Complete Complementary and Genomic DNA Sequences of Human Serum Amyloid P Component", *J. Biochem.* 100, 849-858 (1986).

*Primary Examiner*—David J. Isabella
*Attorney, Agent, or Firm*—Birch, Stewart, Kolasch & Birch

[57] ABSTRACT

The present invention is directed to a human serum amyloid P component peptide sequence having 12 ammo acid residues and having the sequence identified as Glu-Lys-Pro-Leu-Gln-Asn-Phe-Thr-Leu-Cys-Phe-Arg. The invention is also directed to fragments of the above peptide. Two fragments useful in the present invention have the sequence Phe-Thr-Leu-Cys-Phe-Arg and Leu-Cys-Phe-Arg. The above peptides are useful for attaching cells to substrates such as ceramics, tissue culture, dishes, polymers or enamels and thus are useful as research tools for studying particular cells. The above peptides are also useful in vivo as artificial organ replacements which attach surrounding natural cells.

16 Claims, 2 Drawing Sheets

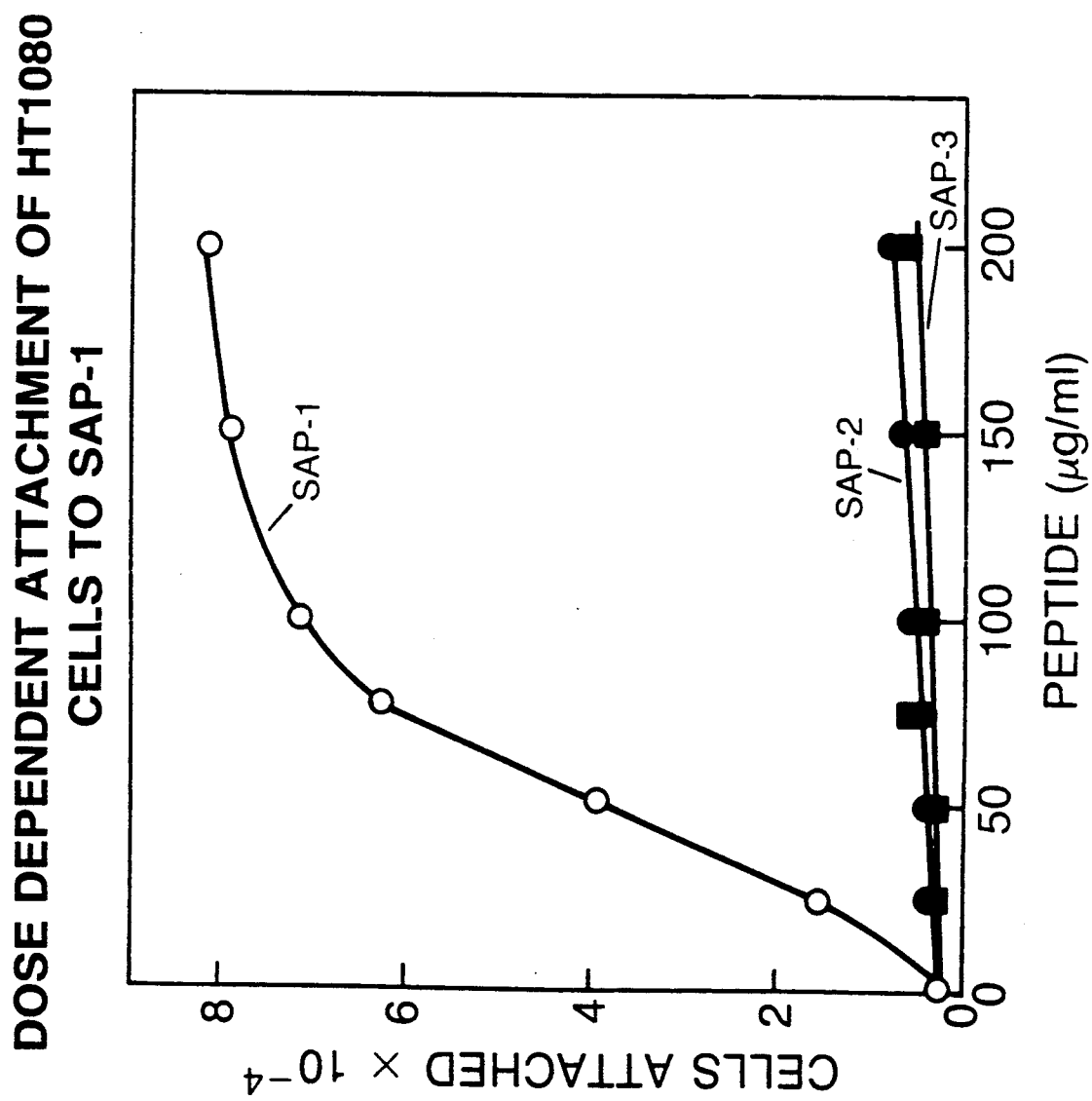

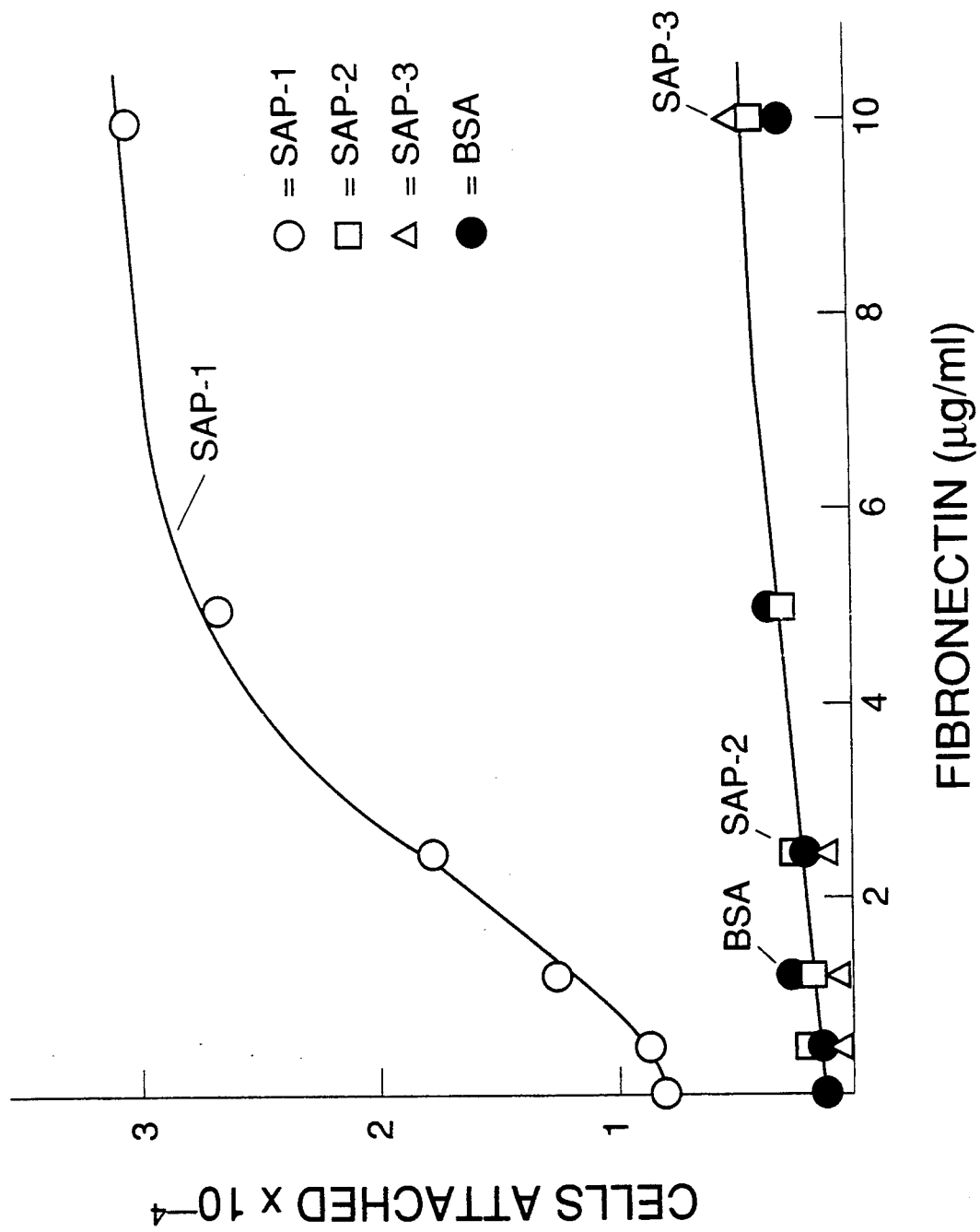

CELL ATTACHMENT PEPTIDES DERIVED FROM AMYLOID P COMPONENT

This invention is directed to the peptides related to amyloid P component which interact with a variety of cell surfaces and promote cell attachment thereto.

BACKGROUND OF THE INVENTION

Amyloid P component is a 125 kDa molecular weight glycoprotein found in serum and in all types of amyloid deposits. In addition to being a normal serum protein, AP is also found in a variety of tissues. Using immunohistochemical techniques, a form of AP has been shown to be localized to normal human glomerular basement membranes, to alveolar capillary walls in sections of normal lung, and to linear intercellular structures in both cardiac and smooth muscle. Although the physiological ligand for AP in amyloid tissue is unknown, binding of AP to amyloid tissue appears to take place via the $Ca^{2+}$-dependent association of AP to heparin sulfate and/or dermatan sulfate, both minor but significant constituents of amyloid tissue. Recent studies have shown that AP is also found in association with heparin sulfate proteoglycans in cerebral amyloidosis of Alzheimer's patients. Detailed studies on the AP found in the glomerular basement membrane indicate that this form of AP is heterogeneous in nature and can only be extracted from the basement membrane by collagenase treatment. Thus, on the basis of these findings, basement membrane AP is believed to be linked to collagen or to some other integral basement membrane component(s).

SUMMARY OF THE INVENTION

The present invention is directed to a human serum amyloid P component peptide sequence having 12 amino acid residues and having the sequence identified as Glu-Lys-Pro-Leu-Gln-Asn-Phe-Thr-Leu-Cys-Phe-Arg. The invention is also directed to a peptide which includes the above peptide or fragments of the above peptide which exhibit cell attachment activity. Two sub-fragments useful in the present invention have the sequence Phe-Thr-Leu-Cys-Phe-Arg and Leu-Cys-Phe-Arg. The above peptides are useful for attaching cells to substrates such as ceramics, tissue culture dishes, polymers or enamels and thus are useful as research tools for studying particular cells. The above peptides are also useful in vivo as artificial organ replacements which attach surrounding natural cells.

The peptide of the present invention also promotes cell attachment activity in the presence of fibronection. That is, the addition of fibronection to the peptide enhances cell attachment.

The invention is also directed to a method of promoting cell attachment to a substrate which comprises:

(a) coating a substrate with a dodecapeptide having the sequence Glu-Lys-Pro-Leu-Gln-Asn-Phe-Thr-Leu-Cys-Phe-Arg (hereinafter referred to as SAP-1) or a peptide which includes said dodecapeptide, or a fragment of said dodeopeptide, to form a peptide coated substrate; and (b) contacting a cell to said peptide coated substrate to promote cell attachment.

The invention is further directed to a substrate for immobilizing cells which comprises a substrate and a peptide as discussed above.

The invention is further directed to a prosthetic device having a surface to which there is linked a dodecapeptide having the formula as discussed above.

Examples of substrates useful in carrying out the cell attachment but in no way limiting, are ceramics, tissue culture dishes, and polymers such as polyvinyl chloride, polyethylene glycol and polystyrene, all of which can be obtained from DuPont Chemical Company. A preferred substrate is plastic.

Examples of cells useful in cell attachment include, but are not limited to, fibroblasts, osteoblasts, fibrosarcoma, melanoma, and neuroblastoma cells.

Examples of the surfaces of prosthetic devices useful for cell attachment are a portion of a vascular graft, a synthetic resin fiber, a percutaneous device. Examples of synthetic resin fibers include nitrocellulose, a polyester, or polyethylene terephthalate.

The density range requirements of the peptide to cell type will vary from cell type to cell type and is readily ascertainable to those skilled in the art.

BRIEF DESCRIPTION OF THE DRAWINGS

FIG. 1 is a graph which discloses the effects of various concentrations of SAP-1 on cell attachment activity, when compared with two other indiscriminate peptides which have been labeled as SAP-2 and SAP-3 used as controls.

FIG. 2 is a graph which discloses the effects of various concentrations of fibronection bound to SAP-1 on cell attachment activity when, compared with two other indiscriminate peptides which have been labeled as SAP-2 and SAP-3 and BSA (bovine serum albumin) used as controls.

DETAILED DESCRIPTION OF THE PREFERRED EMBODIMENTS

Materials and Methods

All references discussed herein below are incorporated by reference. All percentages are by weight unless expressly stated to the contrary.

The nomenclature used to define the dodecapeptide is that specified by Schroder & Lubke, "The Peptides", Academic Press (1965) wherein, in accordance with conventional representation the N-terminus appears to the left, and the C-terminus appears to the right. Where the amino acid residue has isomeric forms, it is the L-form of the amino acid that is represented.

The dodecapeptide, or a fragment thereof, can be synthesized by any suitable method, such as by exclusively solid-phase techniques, by partial solid-phase techniques, by fragment condensation or by classical solution addition. Moreover, synthesis may be carried out by recently developed recombinant DNA techniques.

Common to chemical syntheses of peptides is the protection of the labile side-chain groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino-protecting group to allow subsequent reaction to take place at that location. Accordingly, it is common that, as a step in the synthesis, an intermediate compound is produced which includes each of the amino acid residues located in the desired sequence in the peptide chain with various of these residues having side-chain protecting groups. These protecting groups are then commonly removed substantially at the same time so as to produce the desired resultant product following purification.

The dodecapeptide is preferably prepared using solid phase synthesis, such as that described by Merrifield, *J. Am. Chem. Soc.* 85,2149 (1964), although other equivalent chemical syntheses known in the art, as mentioned above, can also be used. Solid-phase synthesis is commenced from the C-terminus of the peptide by coupling a protected-amino acid to a suitable resin, as generally set forth in U.S. Pat. No. 4,244,946, issued Jan. 21, 1982 to Rivier et al., the disclosure of which is incorporated herein by reference. Examples of syntheses of this general type as set forth in U.S. Pat. Nos. 4,305,872 and 4,316,891. Discussion of the solid-phase synthesis of a 41-residue polypeptide is set forth in *Science* 213, 1394–1397 (September, 1981) in an article by Vale et al., which refers to a more detailed discussion of the synthesis, which appears in an article by Marki et al. in *J. Am. Chem. Soc.* 103,3178 (1981).

After the desired amino acid sequence has been completed, the intermediate peptide is removed from the resin support by treatment with a conventional reagent, such as liquid HF, which not only cleaves the peptide from the resin, but also cleaves all the remaining side-chain-protecting groups. The dodecapeptide can then be purified by gel permeation followed by semipreparative HPLC, as described in Rivier et al., *Peptides: Structure and Biological Function* (1979) pp. 125–128. A purity of at least 95% or higher (based upon all peptides present) is reasonably obtainable and is preferred for clinical testing and/or use. Purity of 95% is practical; however, for certain in vitro applications, lower purity may be acceptable. Accordingly, the dodecapeptide of the present invention is considered useful when it is in substantially pure form which for purposes of this application means at least about 50 weight percent, based upon all peptides present.

The dodecapeptide or biologically active fragments thereof can be used as a cell-attachment substance to provide substrates to which cells will attach by treating a hydrophobic surface, such as an untreated synthetic plastic resin material, e.g., nitrocellulose, or a comparable material, with the peptide. A similar substrate for cell attachment can be generated by coupling the dodecapeptide covalently to a solid support, such as glass or a synthetic plastic resin or a long chain polysaccharide, such as agarose, containing a reactive group that can bind the dodecapeptide. This is accomplished by coupling the peptide to cyanogen bromide-activated agarose beads (sold under the trademark Sepharose by Pharmacia Fine Chemicals, Uppsala, Sweden), and sterilizing the beads by autoclaving.

It is expected that such substrates are useful in cell cultures where it is desirable to ensure proper attachment of the cells.

It is also anticipated that medical devices can be designed making use of such substrates to attract cells to the surface in vivo or to promote growth of a desired cell type on a particular surface prior to grafting. An example of such an approach would be the induction of endothelial cell growth on a prosthetic blood vessel or vascular graft, which is generally woven or knitted from polyester fiber, particularly Dacron fiber (a polyethylene terephthalate). Most types of cells are attracted to fibronectin and to this dodecapeptide, but endothelial cells and fibroblastic cells in particular are attracted to fibronectin and to the dodecapeptide of the present invention. The latter point indicates the potential usefulness of this defined dodecapeptide in coating a patch graft or the like for aiding wound closure and healing following an accident or surgery. The dodecapeptide of the present invention is also of value in coating surfaces of a prosthetic device which is intended to serve as a temporary or semipermanent entry into the body, e.g. into a blood vessel or into the peritoneal cavity, sometimes referred to as a percutaneous device.

All percentages utilized in the methods are by weight unless expressly so stated.

EXAMPLE 1

SYNTHESIS OF PEPTIDES

Serum amyloid P component-derived peptides were synthesized as amides using an automated Model 430A Synthesizer (Applied Biosystems, Inc., Foster City, Calif.) according to the procedure described in Graf et al., *Biochemistry* 26, 6896-6900 (1987). Deprotection and release of the peptides from the solid-phase support matrix was accomplished by treatment with anhydrous HF containing 10% thioanisole or 10% anisole for 1-2 h at $-5°-0°$ C. The composition of the peptides were determined by amino acid analyses and purity was established by high-performance liquid chromatography (HPLC). The oligo-peptides of ten amino acids or larger were purified by HPLC, whereas the oligo-peptides of six amino acids or less were found to be pure enough (greater than 90%) and used without further purification. Less pure peptides (50% or less) contained full biological activity and therefore could be used in various practical applications in the present invention.

EXAMPLE 2

Cell Culture

All cell types used were obtained from American Type Culture Collection, Rockville, Md. and were maintained in Dulbecco's modified Eagle's medium (DMEM) supplemented with 10% fetal calf serum (FCS). The cells were grown to approximately 80% confluency in Falcon T75 flasks. For cell attachment assays, cells were washed with PBS (pH 7.4), and then detached from the tissue culture flasks with 0.025% trypsin, 0.025% EDTA.

The cells were sedimented by low speed centrifugation, suspended in serum-free Eagle's minimal essential medium (EMEM) containing 0.05% BSA and used immediately in the cell attachment assays.

EXAMPLE 3

Cell Attachment Assay

Cell attachment was assayed as described by Graf et al., *Biochemistry* 26, 6896-6900 (1987). 24 well plastic culture plates (Linbro, Flow Laboratories, Inc., Va.) were coated with the desired peptides at 25° C. for 16 h in 0.1M bicarbonate buffer, pH 9.6. Exposed non-specific cell attachment sites were blocked by coating the wells with 3% BSA for 1 h at 25° C. Cells, $(1.1 \times 10^5)$, prepared as described above, were added to each well and incubated at 37° C. for 1 h in a humidified incubator with 5% $CO_2$—95% air mixture. At the end of incubation, plates were gently washed twice with PBS to remove unattached cells. Attached cells were treated with trypsin and electronically counted. Each assay was carried out in duplicate, and the results did not differ by more than 10%. Each peptide was tested for cell attachment in six separate experiments.

EXAMPLE 4

Amyloid P component was isolated from normal human serum using a column filled with DNA-cellulose (Sigma) by the procedure set forth in Pepys et al., *Biochem. Biophys. Res. Commun.* 148:308–313 (1987). Briefly, 500 ml normal human serum was passed through a 1.0×10 cm column of DNA cellulose and the column was washed exhaustively with 50 mM Tris buffer, pH 7.4 containing 150 mM NaCl and 2 mM $CaCl_2$. The crude AP was eluted with 50 mM Tris buffer, pH 7.4 containing 150 mM NaCl and 20 mM EDTA. Purified AP was obtained by using a strong anion exchange HPLC column (DuPont, Wilmington, Del.). Briefly, the column was equilibrated in 10 mM $Na_2HPO_4$ buffer, pH 7.4. AP was eluted with the same buffer run with a linear gradient of NaCl of from 0 to 1M over a period of 30 min. Protein determination was performed according to the procedure of Peterson, *Anal. Biochem.* 83, 346–356 (1977).

Hereinbelow is the sequence of AP and the various peptides named SAP-1, SAP-2, and SAP-3, from amyloid P component which were synthesized according to the method of Example 1 and tested for their ability to promote cell attachment.

```
                                                           15
his thr asp leu ser gly lys val phe val phe pro arg glu ser

|────────>30
val thr asp his val asn leu ile thr pro leu |glu lys pro leu

<── SAP-1 ───────────────|           45
gln |asn phe thr |leu cys phe arg| ala tyr ser aso leu ser arg 60
ala tyr ser leu phe ser tyr asn thr gln gly arg asp asn glu

|──────── SAP-2 ────>75
leu leu val tyr lys glu arg |val gly glu tyr ser leu try ile <──|                                                       90
gly arg| his lys val thr ser lys val ile glu lys phe pro ala 105
pro val his ile cys val ser trp glu ser ser ser gly ile ala

|────────────SAP-3─────────|          120
glu phe trp ile| |asn gly thr |pro leu val lys lys |gly leu arg 135
gln gly tyr phe val glu ala gln pro lys ile val leu gly gln 150
glu gln asp ser tyr gly gly lys phe asp arg ser gln ser phe 165
val gly glu ile gly asp leu tyr met trp asp ser val leu pro 180
pro glu asn ile leu ser ala tyr gln gly thr pro leu pro ala 195
asn ile leu asp trp gln ala leu asn tyr glu ile arg gly tyr val ile ile lys pro leu val trp val    204
```

Referring to FIG. 1 the effects of various concentrations of SAP-1 on cell attachment are depicted. The attachment of cells to SAP-1 increased with respect to the peptide concentration and reached a near maximum at approximately 100 ug/ml of peptide.

Referring to FIG. 2 the attachment of cells to the peptides in presence of fibronectin are depicted. Polystyrene plates were coated with peptides. After blocking the uncovered nonspecific sites with 3% BSA, fibronectin at indicated concentrations was added to peptide-coated plates and incubated at 37° C. After being washed, the cells were added to these plates and allowed to attach at 37° C. for 10 minutes. Preincubation of fibronectin with SAP-1 enhanced the cell attachment. Control peptides and the negative control (bovine serum albumin preincubated with fibronectin) did not show significant cell attachment.

Experiment I

Tissue culture plates (obtained from Linbro, Flow Laboratories, Inc., Va.) were coated with peptides or proteins at 20M. Before coating (a) AP was denatured with 6M Guanidine HCl (GnHCl) for 2 h at 4° C. GnHCl was removed by extensive dialysis against 0.1M bicarbonate buffer, pH 9.6 at 4° C.; (b) AP was heat-denatured at 100° C. for 15 min.; (c) native AP was reduced and the free sulfhydryl groups were blocked by carboxymethylation, and (d) heat-denatured AP was treated as in (c). The values are expressed as the average ± SEM, and are reported hereinbelow in Table I.

TABLE I

| Cell attachment activity of synthetic peptides from amyloid P component. | |
|---|---|
| Peptide/protein | No. attached cells |
| SAP-1 | 15310 ± 817 |
| SAP-2 | 4175 ± 515 |
| SAP-3 | 2427 ± 267 |
| Native SAP | 3125 ± 348 |
| GnHCl-Denatured SAP (a) | 3835 ± 424 |
| Heat-Denatured SAP (b) | 3926 ± 552 |
| Reduced (native)/ carboxy-methylated (c) | 2558 ± 428 |
| Reduced (heat-denatured SAP)/ carboxymethylated (d) | 3436 ± 396 |

The ability of peptides derived from AP to attach to cells was compared with the parent protein isolated from normal human serum. Both peptides and the purified AP were coated onto the assay plates at the same molar concentration (20 uM). The results of these experiments show that only SAP-1 is able to promote the cell attachment. Neither native nor denatured AP nor any of the other peptides, supported cell attachment activity.

Experiment II $1 \times 10^5$ cells were incubated with SAP-1 peptide coated in the wells of plastic tissue culture plates (obtained from Linbro, Flow Laboratories, Inc., Va.) at a concentration of 100 ug/ml and the fractions of cells attached to the peptide were calculated. Plates were also treated with the coating buffer in the absence of SAP-1 and served as the blank. Other experimental conditions are the same as described earlier. All the values represented in the below Table II were obtained after subtracting the respective blanks.

TABLE II
Attachment of various cell types to SAP-1.

| Cell type | % cells attached |
| --- | --- |
| Human osteoblasts | 85 |
| Human skin fibroblasts | 81 |
| RD-ES (Ewing's sarcoma) | 81 |
| A-498 (Kidney sarcoma) | 75 |
| SK-N-MC (Neuroblastoma) | 73 |
| HT-1090 (Fibrosarcoma) | 69 |
| BHK (Fibroblasts, baby hamster kidney) | 68 |
| BT-20 (Breast carcinoma) | 67 |
| Hs 294T (Melanoma human) | 63 |
| B16F10 (Melanoma, mouse) | 73 |

A variety of cells were tested for their adhesivity to SAP-1. All of the cell types studied including normal skin fibroblasts, human osteoblasts, human neuroblastoma and melanoma cells showed significant attachment (65-85% of total) to SAP-1.

Cell attachment activity of the peptide SAP-1 is observed with a variety of cells. Of the cells we tested, many spread after their attachment to SAP-1.

EXPERIMENT III

In order to determine the smallest peptide within SAP-1 capable of supporting cell attachment, several portions of the peptide with and without substitution were synthesized and tested. The results are summarized in Table III hereinbelow.

TABLE III
Cell attachment activity of various combinations of SAP-1

| Peptide formula | % Activity |
| --- | --- |
| Glu—Lys—Pro—Leu—Gln—Asn—Phe—Thr—Leu—Cys—Phe—Arg | 100$^a$ |
| Glu—Lys—Pro—Leu—Gln—Asn | 4 |
| Phe—Thr—Leu—Cys—Phe—Arg | 83 |
| Phe—Thr—Leu—Cys | 3 |
| Thr—Leu—Cys—Phe | 5 |
| Leu—Cys—Phe—Arg | 28 |

$^a$100% activity represents the attachment of HT-1080 cells to SAP-1.

Approximately 83% of the total activity of the original dodecapeptide was confined to a hexapeptide, Phe-Thr-Leu-Cys-Phe-Arg. Other peptides showed less activity.

The dodecapeptide can be modified or changed at the free acid terminal, i.e., amidated or substituted by some other acceptable groups. The peptide can also be modified by replacing Ser with Cys without possibly abolishing the cell attachment activity.

While the invention has been described with regard to certain preferred embodiments, it is understood that a longer peptide containing the dodecapeptide and various other changes and modifications may be made without departing from the scope of the invention which is defined in the following claims.

We claim:

1. A dodecapeptide exhibiting cell attachment activity having the formula Glu-Lys-Pro-Leu-Gln-Asn-Phe-Thr-Leu-Cys-Phe-Arg; or any fragment of said dodecapeptide having cell attachment activity.

2. The peptide according to claim 1, wherein said fragment has the sequence Phe-Thr-Leu-Cys-Phe-Arg.

3. The peptide according to claim 1, wherein said fragment has the sequence Leu-Cys-Phe-Arg.

4. The dedecapeptide of claim 1, in substantially pure form.

5. A method of promoting cell attachment to a substrate which comprises:
   (a) coating a substrate with a dodecapeptide having the sequence Glu-Lys-Pro-Leu-Gln-Asn-Phe-Thr-Leu-Cys-Phe-Arg, a peptide which includes said dodecapeptide, or a fragment thereof having cell attachment activity to form a peptide coated substrate; and
   (b) contacting a cell to said peptide coated substrate to promote cell attachment.

6. The method according to claim 5, wherein said fragment has the sequence Phe-Thr-Leu-Cys-Phe-Arg.

7. The method according to claim 5 wherein said cell is selected from the group consisting of fibroblasts, osteoblasts, fibrosarcoma, melanoma, and neuroblastoma.

8. The method according to claim 5 wherein said substrate is selected from the group consisting of a ceramic, tissue culture dish, enamel or a polymer plastic.

9. The method according to claim 8 wherein said substrate is plastic.

10. A device for immobilizing cells, comprising a substrate and the peptide of claim 1.

11. A prosthetic device having a surface to which there is linked a dodecapeptide having the formula Glu-Lys-Pro-Leu-Gln-Asn-Phe-Thr-Leu-Cys-Phe-Arg, or fragments of said dodecapeptide having cell attachment activity.

12. The prosthetic device according to claim 11 wherein said surface comprises a vascular graft.

13. The prosthetic device in accordance with claim 11 wherein said surface is a synthetic resin fiber.

14. The prosthetic device in accordance with claim 11 wherein said surface a percutaneous device.

15. The prosthetic device in accordance with claim 13 wherein said synthetic resin fiber is selected from the group consisting of a nitrocellulose or a polyester.

16. The prosthetic device in accordance with claim 15 wherein said synthetic resin fiber is a polyethylene terephthalate.

* * * * *